United States Patent [19]

Sibley et al.

[11] Patent Number: 5,128,254
[45] Date of Patent: Jul. 7, 1992

[54] CDNA ENCODING THE LONG ISOFORM OF THE $D_2$ DOPAMINE RECEPTOR

[75] Inventors: David R. Sibley, Rockville; Frederick J. Monsma, Jr., Baltimore; Loris D. McVittie; Lawrence C. Mahan, both of Bethesda, all of Md.

[73] Assignee: The United States of America as represented by the Secretary of the Department of Health and Human Services, Washington, D.C.

[21] Appl. No.: 430,049

[22] Filed: Nov. 1, 1989

[51] Int. Cl.[5] .................. C12N 15/12; C07H 21/04
[52] U.S. Cl. .................................. 435/172.3; 536/27
[58] Field of Search .................... 536/27; 435/172.3

[56] References Cited

PUBLICATIONS

Bunzow, et al., Cloning and Expression of a Rat $D_2$ Dopamine Receptor cDNA, Nature, vol. 336, pp. 783-787, Dec. 22/29, 1988.
Elazar, et al., Association of Two Pertussis Toxin-Sensitive G-Proteins with the $D_2$-Dopamine Receptor from Bovine Striatum, EMBO Journal, vol. 8, No. 8, pp. 2353-2357, 1989.
Mitsuhashi, et al., Regulation of Expression of the Alternative mRNAs of the Rat $\alpha$-Thyroid Hormone Receptor Gene, J. Biological Chemistry, vol. 264, No. 15, pp. 8900-8904; May 25, 1989.

Primary Examiner—John Doll
Assistant Examiner—George C. Elliott
Attorney, Agent, or Firm—Cushman, Darby & Cushman

[57] ABSTRACT

In the present investigation, we report the identification and cloning of a cDNA encoding an RNA splice variant of the rat $D_2$ receptor cDNA[12]. This cDNA codes for a receptor isoform which is predominantly expressed in the brain and contains an additional 29 amino acids in the 3rd cytoplasmic loop, a region believed to be involved with G protein coupling. This is the first example of a novel G-protein coupled receptor isoform generated by alternative RNA splicing.

6 Claims, 7 Drawing Sheets

FIG. I

```
-146 AGGGACGGCGGCCCCGACGGCTGCCGGAGGGGCCGTGCGTGGA
     TGCGGGGGAGCTGGAAGCCTCGAGCAGCCCGGCCCATATGGCTTGAAGAGCCGTGCCACCCAGTGCCCCACTGCCCCA

-99

1  ATG GAT CCA CTG AAC CTG TCC TGG TAC GAT GAC GAT CTG GAG AGG CAG AAC TGG AGC CGG CCC TTC AAT GGG TCA
     Met Asp Pro Leu Asn Leu Ser Trp Tyr Asp Asp Asp Leu Glu Arg Gln Asn Trp Ser Arg Pro Phe Asn Gly Ser   25

76  GAA GGG AAG GCA GAC AGG AGG CCC CAC TAC AAC TAC TAT GCC ATG CTG ATG CTC CTC ATC TTT ATC GTC TTT
     Glu Gly Lys Ala Asp Arg Arg Pro His Tyr Asn Tyr Tyr Ala Met Leu Met Leu Leu Ile Phe Ile Val Phe     50

151  GGC AAT GTG CTG GTG TGC ATG GCT GTA TCC CGA GAG AAG GCT TTG CAG AAG ACC ACC TAC TTG ATA GTC AGC
     Gly Asn Val Leu Val Cys Met Ala Val Ser Arg Glu Lys Ala Leu Gln Lys Thr Thr Tyr Leu Ile Val Ser     75

226  CTT GCT GAT CTT CTG GCC GTG ACA CTG GTA ATG CCG TGG GTT GTC TAC CTG GAG GTG GTG GGT GAG TGG
     Leu Ala Val Ala Asp Leu Leu Ala Val Thr Leu Val Met Pro Trp Val Val Tyr Leu Glu Val Val Gly Glu Trp   100

301  AAA TTC AGC AGG ATT CAC TGT GAC ATC TTT GTC ACT CTG GAT GTC ATG TGC TGC ACA AGC ATC CTG AAC CTG
     Lys Phe Ser Arg Ile His Cys Asp Ile Phe Val Thr Leu Asp Val Met Cys Thr Ala Ser Ile Leu Asn Leu     125

376  TGT GCC ATC AGC ATT GAC AGG TAC ACA GCA GTG GCA ATG CCC ATG CTG TAT AAC ACA CGC TAC AGC TCC AAG CGC
     Cys Ala Ile Ser Ile Asp Arg Tyr Thr Ala Val Ala Met Pro Met Leu Tyr Asn Thr Arg Tyr Ser Ser Lys Arg   150

451  CGA GTT ACT GTC ATG ATT GCC ATG ATT GTC TGG GTC CTG TCC TTC ACC ATC TCC TGC CCA CTG CTC TTC GGA CTC AAC
     Arg Val Thr Val Met Ile Ala Ile Val Trp Val Leu Ser Phe Thr Ile Ser Cys Pro Leu Leu Phe Gly Leu Asn   175

526  AAT ACA GAC CAG AAT GAG TGT ATC ATT GCC AAC CCT GCC TTT GTG GTC TAC TCC TCC ATT GTC TCA TTC TAC GTG
     Asn Thr Asp Gln Asn Glu Cys Ile Ile Ala Asn Pro Ala Phe Val Val Tyr Ser Ser Ile Val Ser Phe Tyr Val   200

601  CCC TTC ATC GTC ACT CTG CTG GTC TAT ATC CAG ATC TAC ATC GTC CTC CGG AAG CGC CTC ACA CGG GTC AAC ACC
     Pro Phe Ile Val Thr Leu Leu Val Tyr Ile Lys Ile Tyr Ile Val Leu Arg Lys Arg Lys Val Asn Thr   225

676  AAG CGC AGT AGT GCT TTC GGA CGT TTC AGA GCC AAC CTG AAG ACA CCA AAG CTG GGC AAC TGT ACC CAC CCT GAG GAC ATG
     Lys Arg Ser Ser Ala Phe Gly Arg Phe Arg Ala Asn Leu Lys Thr Pro Lys Leu Gly Asn Cys Thr His Pro Glu Asp Met 250

751  AAA CTC TGC ACC GTT ATC ATG AAG TCT AAT GGG AGT TTC CCA GTG AAC AGG CGG AGA ATG GAT GCT GCC CGC CGA
     Lys Leu Cys Thr Val Ile Met Lys Ser Asn Gly Ser Phe Pro Val Asn Arg Arg Arg Met Asp Ala Ala Arg Arg   275
```

FIG. 1(CONT-1)

```
826  GCT CAG GAG CTG GAA ATG GAG ATG CTG TCA AGC ACC AGC CCC CCA GAG AGG ACC CGG TAT AGC CCC ATC CCT CCC  300
     Ala Gln Glu Leu Glu Met Glu Met Leu Ser Ser Thr Ser Pro Pro Glu Arg Thr Arg Tyr Ser Pro Ile Pro Pro

901  AGT CAC CAG CTC ACT CTC CCT GAT CCA TCC CAC CAC GGC CTA CAT AGC AAC CCT GAC AGT CCT GCC AAA CCA  325
     Ser His Gln Leu Thr Leu Pro Asp Pro Ser His His Gly Leu His Ser Asn Pro Asp Ser Pro Ala Lys Pro

976  GAG AAG AAT GGG CAC GCC AAG ATT GTC ATT CCC AGG ATT GCC AAG CTC TTT GAG ATC CAG ACC ATG CCC AAT GGC  350
     Glu Lys Asn Gly His Ala Lys Ile Val Asn Pro Arg Ile Ala Lys Phe Glu Ile Gln Thr Met Pro Asn Gly

1051 AAA ACC CGG TCC CTT AAG ACG ATG AGC CGC AGA AAG CTC TCC CAG CAG AAG GAG AAA GCC ACT CAG ATG  375
     Lys Thr Arg Ser Leu Lys Thr Met Ser Arg Arg Lys Leu Ser Gln Gln Lys Glu Lys Ala Thr Gln Met

1126 CTT GCC ATT GTT CTC GGT GTG TTC ATC ATC ACG CAC ATC CTG AAT ATA CAC TGT  400
     Leu Ala Ile Val Leu Gly Val Phe Ile Ile Thr His Ile Leu Asn Ile His Cys

1201 GAT TGC AAC ATC CCA GTC CTC TAG AGC GCC TTC ACA TGG CTG TAT GTC AAC AGT GCC GTC AAC CCC ATC  425
     Asp Cys Asn Ile Pro Val Leu Tyr Ser Ala Phe Thr Trp Leu Tyr Val Asn Ser Ala Val Asn Pro Ile

1276 ATC TAC ACC ACC TTC AAC ATC GAG TTC CGC AAG TTC ATG AAG ATC TTG CAC TGC TGAGTCTGCCCCTTGCCTGCACAG  444
     Ile Tyr Thr Thr Phe Asn Ile Glu Phe Arg Lys Phe Met Lys Ile Leu His Cys
```

FIG. 1 (CONT-2)

```
1357  CAGCTGCTTCCCACCTCCCTGCCTATGCAGGCCAGACCTCATCCCTGCAAGCTGTGGGCAGAAAGGCCCAGATGGACTTGGCCTTCTCTGACCCTGCAG
1457  GCCCTGCAGTGTTAGCTTGGCTCGATGCCCCTCTGCCCACACACCCTCATCCTGCCAGGGTAGGCCAGGGAGACTGGTATCTTACCAGCTCTGGGGT
1557  TGGACCCATGGCTCAGGGCAGCTCACAGAGTGCCCCTCTCATATCCAGACCCTGTCTCCTTGGCACCAAAGATGCAGCGGCCTTCCTTGACCTTCCTCTT
1657  GGGCACAGAAACTAGCTCAGTGGTCGAGCACACCTGCTGCTTGCCCCTTGCCTGCCTGTGCCAGATCAGGTGGTGGGAGGAGCAACAG
1757  TTCTTACTTTATAGGAACCACATAGGAAAGCAGGAACACGCCAAGTCCTCCAGCAACATCAGTGTCAGGAGACACACATAAACACCAGTAGTCCAT
1857  GGACCCCAGAGAAACTGAGGCTGAAAAATCTGTTTCCACTCTAGTGTGAGTCCCTACTTTTCATAGCCATGGTATTACTATGTCCTACCTTG
1957  TTTATAGTATCCCATGGGTTTCTGTACCCTTTGGGGAAAACAACTCTAATCCTCAAGGGCCCCAAGAGAATCTGTAAGGAGAAAAATAGGCTGATCTCC
2057  CTCTACTCTCCAATCCACTCCACCACTTCTTGATATACCTTGGATGTATCCATTCCTCACAGCAAATGCTGCCCAGTCAGGCCTTGGACCAGTGTTGGAG
2157  TTGAAGCTGGATGTGGTAACTTGGGCTCTTTGGGCTCTTGGGGGGTTGTTAACATCGTCTCTCTTCCATATCTCTTCCCAGTGCCTCTGCCTTAGA
2257  AGAGGCTGTGATGGGGTGCTGGGACTGCTGATACCATTGGGCCTGGCCCTGAATGAGGAGGGGAAGCTGCAGTTTGGAGGGTTCTGGGATCCAACTCTG
2357  TAACATCACTATACCTGCACCAAAACTAATAAAACCTTGACAAGAGTCAAAAAAAAAA
                                                            2404
```

1 2 3 4 5 6 7 8 9 10

1 2 3 4 5 6 7 8 9 10

5,128,254

CDNA ENCODING THE LONG ISOFORM OF THE D₂ DOPAMINE RECEPTOR

BACKGROUND OF THE INVENTION

The present invention relates to a DNA segment encoding a long isoform of a mammalian $D_2$ dopamine receptor having a sequence of 29 amino acids that is absent in the known isoform of this receptor.

Dopamine receptors belong to a large class of neurotransmitter and hormone receptors which are linked to their signal transduction pathways via guanine nucleotide binding regulatory (G) proteins. Pharmacological, biochemical and physiological criteria have been used to define two subcategories of dopamine receptors referred to as $D_1$ and $D_2$[1]. $D_1$ receptors are associated with the activation of adenylyl cyclase activity[2] and are coupled with the $G_s$ regulatory protein[3]. In contrast, activation of $D_2$ receptors results in various responses including inhibition of adenylyl cyclase activity[4], inhibition of phosphatidylinositol turnover[5], increase in K+ channel activity[6] and inhibition of $Ca^{2+}$ mobilization[7]. The G protein(s) linking the $D_2$ receptors to these responses have not been identified, although $D_2$ receptors have been shown to both co-purify[8,9] and functionally reconstitute[10,11] with both "$G_i$" and "$G_o$" related proteins[3]. One means of achieving the diversity of second messenger pathways associated with $D_2$ receptor activation would be the existence of multiple $D_2$ receptor subtypes, each being coupled with a different G protein-linked response. Efforts towards elucidating $D_2$ receptor diversity were recently advanced by the cloning of a cDNA encoding a rat $D_2$ receptor[12]. This receptor exhibits considerable amino acid homology with other members of the G protein-coupled receptor super-family for which cDNAs and/or genes have been cloned[12,13].

SUMMARY OF THE INVENTION

The present invention relates to a DNA segment encoding a long isoform of a mammalian $D_2$ dopamine receptor having a sequence of 29 amino acids that is absent in the known isoform of this receptor. This "long" isoform is the predominant species in mammalian tissues that are populated by $D_2$ dopamine receptors. In a principal embodiment, a recombinant DNA molecule comprising cDNA clone of the rat long isoform of this receptor and an expression vector is used to transfect eukaryotic cells which results in expression of this receptor on those cells. According to the present invention, receptors of this isoform, either in isolation or incorporated in cell membranes, are used for screening and developing drugs for selective activity on this dopamine receptor long isoform.

Further, the present embodiment of the DNA segment of this invention, which encodes the rat $D_2$ receptor long isoform, can be used for a nucleic acid probe in hybridization methods according to this invention to obtain molecular clones of DNA segments encoding the homologous receptors of this same isoform from any other mammalian species.

The present invention may be understood more readily by reference to the following detailed description of specific embodiments and the Figures included therein, which illustrate the following:

BRIEF DESCRIPTION OF THE FIGURES

FIG. 1. Nucleotide and deduced amino acid sequence of the $D_2$ recptor cDNA clone. The 87 bp/29 amino acid insertion sequence is indicated by underlining. The nucleotide sequence is numbered beginning with the initiator methionine and indicated at the left of each line. The amino acid numbers are indicated at the right of each line. The single base differences in the 3' untranslated sequence are indicated by dots.

DESCRIPTION OF SPECIFIC EMBODIMENTS

Figure 2A:
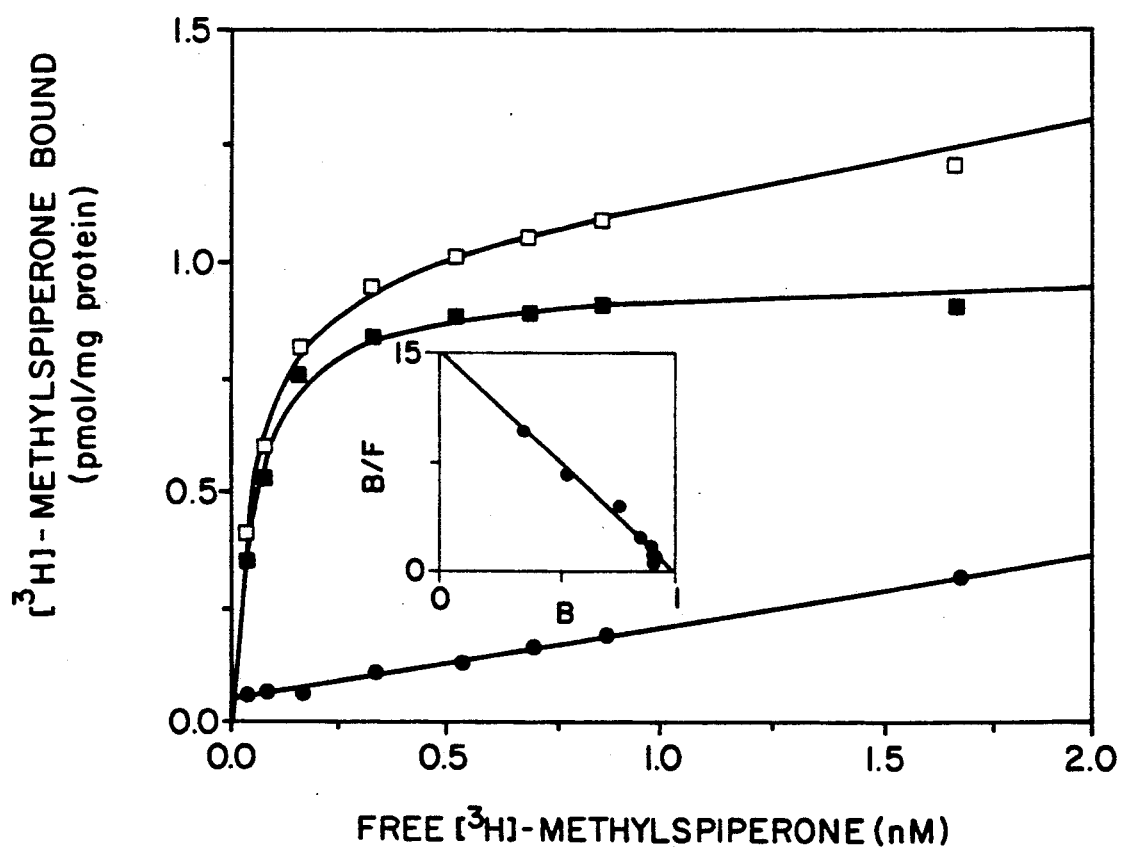
FIG. 2, A and B. Expression of the $D_2$ receptor cDNA in COS-7 cell membranes assayed with [³H]methylspiperone binding. A, Saturation isotherms of the total (□), nonspecific (●), and specific (○) binding of [³H]methylspiperone to transfected COS-7 cell membranes. The inset shows a Scatchard transformation of the specific binding data. In this experiment, which was representative of three, the calculated $K_D$ and $B_{max}$ values were 64.1 pM and 0.97 pmol/mg protein, respectively. B, Competition analysis of various dopaminergic ligands for [³H]methylspiperone binding in COS-7 cell membranes. In this experiment, [³H]methylspiperone (0.6 nM) was incubated with increasing concentrations of the following ligands; spiperone (▲), (+)butaclamol (△), (−)sulpiride (■), dopamine (●), SCH-23390 (□), and (−)butaclamol (○). Average $K_i$ and SEM values from 3 experiments are given in the text.

As part of an effort to isolate cDNAs encoding dopamine receptor subtypes, we initially constructed a λ ZAP II cDNA library using mRNA purified from rat striatum, the region of the brain known to contain the highest levels of both $D_1$ and $D_2$ dopamine receptors[1]. Poly (A)+ RNA was isolated from rat striatal tissue using standard procedures[19] and used to construct a cDNA library in the λ ZAP II vector (Stratagene, La Jolla, Calif.). The resulting library contained $6.1 \times 10^6$ independent recombinants. $1 \times 10^6$ recombinants from the unamplified library were screened using the oligonucleotide 5'-GATGAAGAAGGGCAGCCAG-CAGATGATGAACACA(G)CC-3' radiolabeled using [γ-32P]ATP and T4 polynucleotide kinase. Duplicate nitrocellulose filters were hybridized in 0.3M NaCl/0.03M sodium citrate (2X SSC), 0.02M Na2HPO4, 0.1% SDS, 0.2 mg/ml salmon sperm DNA, and 4×10^6 dpm/ml of 32P-labeled probe for 18 hr at 42° C. High stringency washing of the filters was performed with 0.5X SSC and 0.1% SDS at 60° C. prior to autoradiography. λ phage found to hybridize to the probe were subsequently plaque purified. In vivo excision and rescue of the nested pBluescript plasmids from the λ ZAP II clones were performed using helper phage according to the Stratagene protocol. Nucleotide sequence analysis was performed using the Sanger dideoxy nucleotide chain termination method on denatured doubled-stranded plasmid templates with Sequenase (US Biochemical Corp.). Primers were synthetic oligonucleotides which were either vector-specific or derived from prior sequence information. In some cases a series of nested deletion mutants were constructed using the Exo III/Mung Bean nuclease procedure (Stratagene) prior to DNA sequencing.

This library was screened with a mix of two 36 mer synthetic oligonucleotides, the sequence of which was derived from amino acids 352–363 of the rat $D_2$ receptor cDNA[12]. This region corresponds to the 6th transmembrane spanning domain and is known to exhibit very high homology among previously cloned G protein-coupled receptors[13]. Out of $1\times10^6$ recombinants screened, a total of 15 positive clones were isolated. Restriction analysis and partial sequence information indicated that 5 of these clones were related to the rat $D_2$ receptor cDNA previously reported[12]. One of the clones containing an insert of 2.5 kb was completely sequenced and the nucleotide and deduced amino acid sequence of this cDNA is shown in FIG. 1. The longest open reading frame in this cDNA codes for a 444 amino acid protein with a relative molecular mass Mr=50,887. The nucleotide and amino acid sequence within this coding region is identical to the rat $D_2$ receptor cDNA previously reported with the notable exception of an additional 87 bp sequence coding for a 29 amino acid insertion between residues 241 and 242[12]. This is located within the predicted 3rd cytoplasmic loop approximately 30 amino acids away from the carboxy terminus of the 5th transmembrane spanning domain. In addition to this insertion sequence, and a slightly extended 5' untranslated sequence, we also noted 5 base differences within the 3' untranslated region in comparison with the previously published sequence[12] (FIG. 1). Subsequent sequence analysis indicated that all 5 of the $D_2$ receptor-related cDNAs isolated from this library contained the identical 87 bp insertion sequence. The nucleotide sequences delineating the boundaries of this insertion sequence correspond with consensus exon sequences for RNA splice junctions[14], suggesting that the cDNA resulted from alternative RNA splicing.

In order to confirm the $D_2$ subtype identity of this cDNA clone and to determine if the 29 amino acid insertion sequence results in a major alteration in the ligand binding properties of the $D_2$ receptor, the cDNA was inserted into the SV40 promoter-driven vector, pEUK-C1, for expression in eukaryotic cells.

Figure 2B:
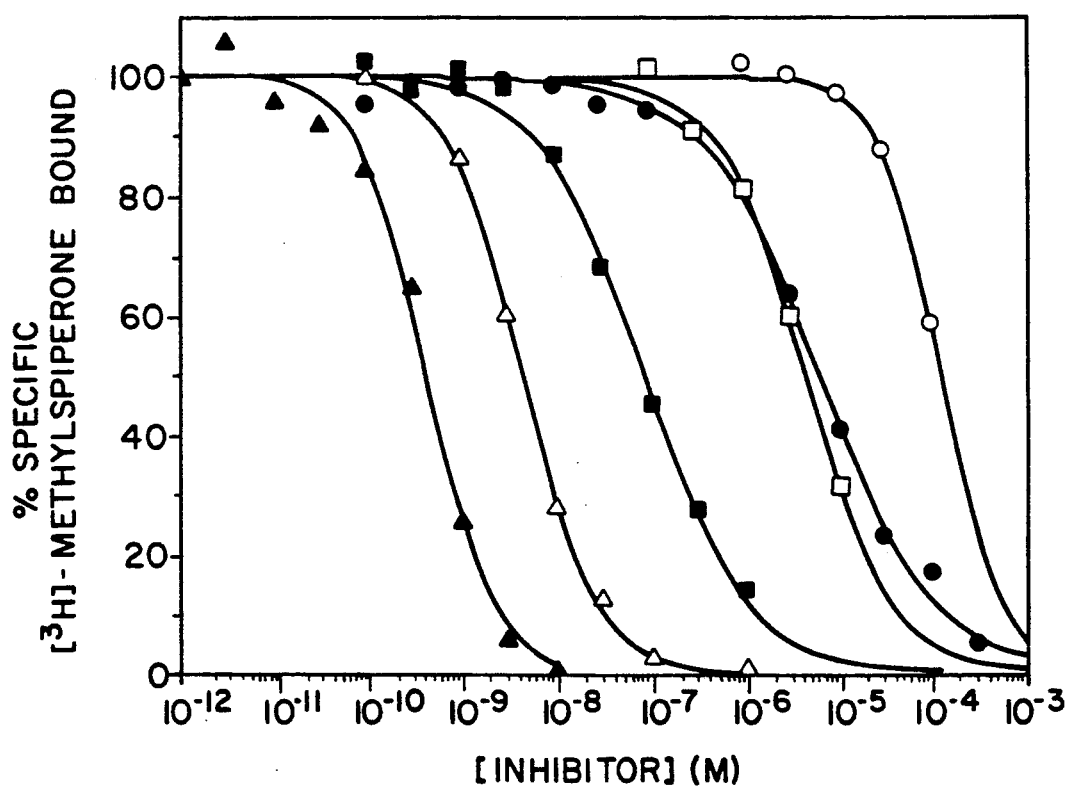

A 2.4-kb Xba I-Xho I fragment containing the entire coding region and most of the $D_2$ receptor cDNA was excised from the pBluescript clone and ligated into the corresponding restriction sites of the pEUK-C1 vector (Clontech, Palo Alto, Calif.) The resulting plasmid, pEUK-D2L, was then transfected into COS-7 cells using a modified CaPO4 precipitation method (Clontech). The cells were treated with 3 mM sodium butyrate after 48 hr and were harvested after 72 hr. Membranes were prepared and assayed for $D_2$ receptor binding activity using [3H]methylspiperone (Dupont/NEN) exactly as previously described[20]. FIG. 2A shows that [3H]methylspiperone bound to the membranes in a saturable fashion with high specific activity ($\approx 1$ pmol/mg protein) and an affinity ($62.1\pm2.1$ pM) in good agreement with that found in the rat striatum[1]. No specific binding activity was detected in COS-7 cells that had not been transfected with pEUK-D2L or transfected with the pEUK-C1 vector alone (data not shown). FIG. 2B demonstrates the ability of a variety of dopaminergic ligands to compete for specific [3H]methylspiperone binding to transfected COS-7 cell membranes. The high affinity $D_2$-selective antagonist, spiperone ($36\pm3.8$ pM) is the most potent agent followed by the non-selective dopaminergic antagonist (+)butaclamol ($0.52\pm0.01$ nM) which is more than 4 orders of magnitude more potent than its inactive isomer, (−)butaclamol (>10 μM). The $D_2$-selective antagonist (−)sulpiride ($7.9\pm0.42$ nM) also exhibits high affinity whereas the $D_1$-selective antagonist SCH-23390 ($0.41\pm0.047$ μM) does not. This rank order of potency as well as the absolute affinities ($K_i$) of the antagonists agree well with those previously demonstrated for $D_2$ receptors[1]. Dopamine is also able to completely inhibit [3H]methylspiperone binding ($K_i=0.71\pm0.012$ μM) although the competition curve is homogeneous (Hill coefficient$\approx 1$) (FIG. 2B) and not significantly affected by guanine nucleotides (data not shown) indicating the absence of appropriate G protein coupling[15] in the COS-7 cells. These experiments indicate that the insertion sequence does not appear to affect the basic properties of ligand recognition for the $D_2$ receptor.

Figure 3A:
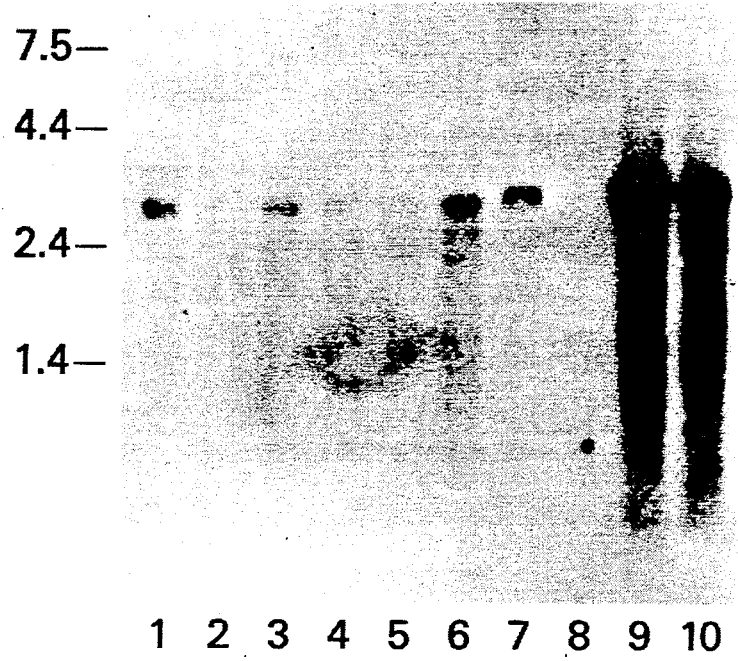
FIG. 3, A and B. Northern blot analysis of $D_2$ receptor transcripts in brain and other rat tissues. Each lane contained 2 μg of poly (A)+RNA. Lanes 1, total brain; 2, cerebellum; 3, cortex; 4, hippocampus; 5, olfactory bulb; 6, mesencephalon; 7, retina; 8, kidney; 9, striatum; 10, pituitary. The gel locations of the RNA size markers (kb) are indicated. A, The blots were hybridized with an oligonucleotide derived from amino acids 10–25 (FIG. 1); 5'-TGACCCATTGAAGGGCCGGCT-CCAGTTCTGCCTCTCCAGATCGTCATC-3'. B, Hybridization was performed with an insert sequence oligonucleotide derived from amino acids 242–257 (FIG. 1): 5'-CATGATAACGGTGCAGAGTTT-CATGTCCTCAGG-GTGGGTACAGTTGCC-3'. This experiment was performed twice with similar results.
Figure 3B:
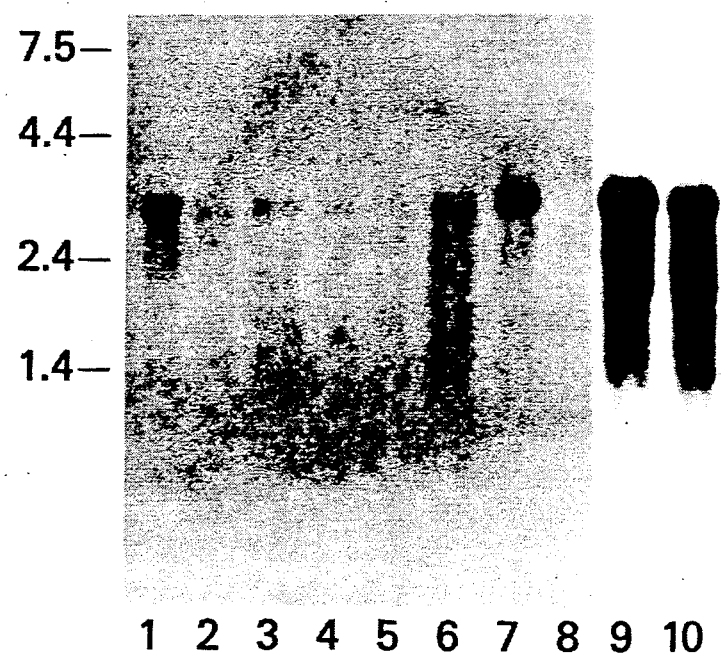

In order to verify the expression of the $D_2$ receptor variant containing the insertion sequence and determine the relative proportions of the two receptor isoforms, we subjected various rat tissues to Northern blot analysis using an oligonucleotide probe to a consensus region (FIG. 3A) as well as an insert sequence-specific probe (FIG. 3B).

Poly (A)+RNA was isolated from rat tissues using standard procedures[19] and run on 1% agarose plus 0.66M formaldehyde gels. After electrophoresis and blotting, the filters were prehybridized in 4X SSPE, 5X Denhardt's, 50% formamide, 250 μg/ml yeast tRNA, 500 μg/ml sheared salmon sperm DNA, and 0.1% SDS for 16 hr at 37° C. The filter blots were then hybridized in the same solution for 18 hr at 37° with $2\times10^6$ dpm/ml oligonucleotide probe radiolabeled with [α-32P]ATP and terminal deoxystransferase. The blots were washed four times in 1X SSPE and 0.1% SDS for 20 min for at 56° C. and twice at room temperature prior to autoradiography.

As shown in FIG. 3, the tissues expressing the highest levels of the 2.9 kb $D_2$ receptor mRNA are the striatum and pituitary. The retina shows a moderate abundance of mRNA with low levels being observed in the mesencephalon and cortex and trace quantities detected in the olfactory bulb and hippocampus. Little to no mRNA was found in the cerebellum and kidney. This tissue distribution corresponds closely to that previously determined for $D_2$ receptor expression[1]. Of greatest interest, however, is the fact that in all of the tissues examined, the amount of mRNA detected with the two probes is very similar (FIG. 3) and in no instance did the consensus probe detect greater quantities of mRNA.

To further investigate the relative distributions of the two mRNAs encoding the $D_2$ receptor isoforms, we performed in situ hybridization analysis in the rat forebrain with the two oligonucleotide probes used in FIG. 3. FIG. 4 shows darkfield photomicrographs of in situ hybridization histochemical localization of $D_2$ receptor mRNA in a coronal section of rat brain which includes the striatum.

Coronal sections through the striatum were cut in a cryostat and adhered to glass slides that had been twice coated with gelatin. Sections were fixed in a 4% paraformaldehyde solution in 0.9% saline for 10 min, rinsed and incubated in a fresh solution of 0.25% acetic anhydride in 0.1M triethanolamine and 0.9% saline (pH 8.0) for 10 min, dehydrated in ethanol and defatted for 2×5 min in chloroform, rehydrated and air dried. These sections were then hybridized with the $^{35}$S-dATP tailed oligonucleotide probes and processed as previously described[21]. Subsequently, the slides were dipped in NTB3 emulsion (diluted 1:1 with water) and exposed for 4-6 weeks, after which they were developed in D-19 developer for 2 min, fixed, rinsed, counterstained with thionin, dehydrated and coverslipped out of xylene.

Figure 4A:
FIG. 4, panels a–c. Darkfied photomicrographs (silver grains appear white) of in situ hybridization histochemical (ISHH) localization of $D_2$ receptor mRNA in a coronal section of rat brain which includes the striatum. Panel a, ISHH labeling using the ³⁵S-labeled oligonucleotide from FIG. 3A. Panel b, ISHH labeling using the ³⁵S-labeled oligonucleotide from FIG. 3B. In both sections the labeling of cells is most dense in the striatum and olfactory tubercle. Panel c, High power magnification of labeling from FIG. 4, panel b showing localization of $D_2$ receptor mRNA in a subset of medium sized neurons in the striatum. Approximately half of the medium sized cells are labeled by this procedure.
Figure 4B:
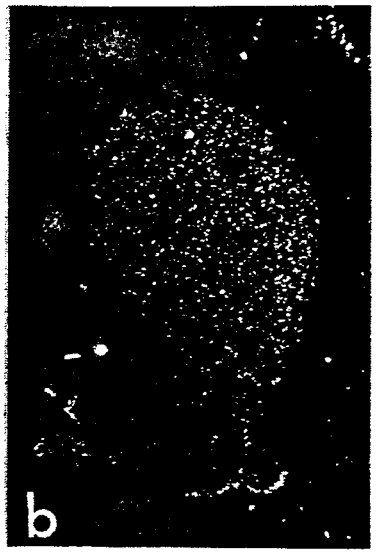
Figure 4C:

As can be seen, identical patterns of labeling were obtained using both the consensus region probe and the insert sequence probe (FIGS. 4a and b). The highest labeling occured in the striatal neurons where about 50% of the medium sized neurons were labeled (FIG. 4c). Larger sized neurons in the striatum also exhibited labeling (data not shown).

It is interesting that in FIGS. 3 and 4, there did not appear to be any difference in the levels of mRNA detected using the two oligonucleotide probes. If any tissue or brain area expressed mRNA containing the insertion sequence at a level equal to or less than the one lacking the insertion, then the consensus probe should detect mRNA levels that are at least 2-fold greater than those seen with the insert probe. These experiments thus indicate that not only is the longer $D_2$ receptor variant (which we propose designating $D_{2L}$) expressed in brain and other tissues, but in those areas which have been examined (especially the striatum), it appears to be the major if not exclusive isoform. Further experiments directed at determining the actual levels of the receptor proteins will be required to confirm this point. At present, the location of predominant expression of the shorter $D_2$ receptor lacking the insertion sequence (now designated $D_{2S}$) is unclear.

With the exception of the visual opsins, the genes for the G protein-coupled receptor family have, in most instances, demonstrated a lack of introns within their coding sequences[13] thus precluding the generation of receptor diversity through alternative RNA splicing. Recently, however, it has been determined that the serotonin 5HT$_{1C}$ (B. J. Hoffman, personal communication) and $D_2$ dopamine[12] receptors are encoded by genes which contain introns. Our current data on the rat $D_2$ receptor now provides the first example of G-protein-coupled receptor isoforms which are generated through alternative RNA splicing. These isoforms are defined by the presence or absence of an internal 29 amino acid sequence within the receptor protein. This variation could have arisen either through the existence of a "cassette exon" or through alternative internal acceptor or donor sites within the precursor mRNA[16].

The isolation and sequencing of the rat $D_2$ receptor gene will be required to distinguish among these possibilities. The location of this optional amino acid sequence is particularly intriguing as it occurs within the predicated 3rd cytoplasmic loop of the receptor[12]. Recent mutagenesis studies using the $\beta_2$-adrenergic catecholamine receptor have indicated that this region is highly involved in G protein-receptor coupling[17,18]. It is thus tempting to speculate that the two $D_2$ receptor isoforms are coupled to different G proteins thus resulting in the diversity of responses associated with $D_2$ receptor activation[4-7]. Further work involving the stable expression of the two $D_2$ receptor isoforms in cells exhibiting appropriate G protein-linked effector systems will be required to test this hypothesis.

BIBLIOGRAPHY

1. Creese, I. & Fraser, C. M., eds., Receptor Biochemistry and Methodology: Dopamine Receptors, Vol. 8, Alan R. Liss, Inc., New York (1987).
2. Kebabian, J. W. et al. Trends Pharmacol. 7, 96-99 (1986).
3. Freissmuth, M., Casey, P. J. & Gilman, A. G. FASEB J. 3, 2125-2132 (1989).
4. Creese, I., Sibley, D. R., Hamblin, M. W. & Leff, S. E. Ann. Rev. Neurosci. 6, 43-71 (1983).
5. Vallar, L. & Meldolesi, J. Trends Pharmacol. 10, 74-77 (1989).
6. Lacey, M. G. Mercuri, N. B. & North, R. A. J. Physiol. 392, 397-416 (1987).
7. Bigornia, L. et al. J. Neurochem. 51, 999-1006 (1988).
8. Senogles, S. E. et al. J. Biol. Chem. 262, 4860-4867 (1987).
9. Elazar, Z., Siegel, G. & Fuchs, S. EMBO J. 8, 2353-2357 (1989).
10. Senogles, S. E., Amlaiky, N., Falardeau, P. & Caron, M. G. J. Biol. Chem. 263, 18996-19002 (1988).
11. Ohara, K. et al. Mol. Pharm. 33, 290-296 (1988).
12. Bunzow, J. R. et al. Nature 336, 783-787 (1988).
13. O'Dowd, B. F., Lefkowitz, R. J. & Caron, M. G. Ann. Rev. Neurosci. 12, 67-83 (1989).
14. Mount, S. M. Nucleic Acids Res. 10, 459-472 (1982).
15. Sibley, D. R., De Lean, A. & Creese, I. J. Biol. Chem. 257, 6351-6361 (1982).
16. Andreadis, A., Gallego, M. E., Nadal-Ginard, B. Ann. Rev. Cell Biol. 3, 207-242 (1987).
17. Strader, C. D., Sigal, I. S. & Dixon, R. A. F. FASEB J. 3, 1825-1832 (1989).
18. O'Dowd, B. F. et al. J. Biol. Chem. 263, 15985-15992 (1988).
19. Okayama, H. et al. Methods Enzymol. 154, 3-28 (1987).
20. Monsama, F. J., Jr., Brassard, D. L. & Sibley, D. R. Brain Res. 492, 214-324 (1989).
21. Gerfen, C. R. & Young, W. S. Brain Res. 460, 161-167 (1988).

For purposes of completing the background description and present disclosure, each of the published articles, patents and patent application heretofore identified in this specification are hereby incorporated by reference into the specification.

The foregoing invention has been described in some detail for purposes of clarity and understanding. It will also be obvious to one of ordinary skill in the art of genetic engineering that various combinations in form and detail can be made without departing from the scope of the invention.

What is claimed is:

1. An isolated DNA segment encoding a long isoform of mammalian $D_2$ dopamine receptor comprising an amino acid sequence 242-270 shown in FIG. 1 of this specification.

2. An isolated DNA segment wherein said segment encodes a long isoform of mammalian $D_2$ dopamine receptor from a rate, said receptor comprising an amino acid sequence 0-444 shown in FIG. 1 of this specification.

3. A DNA segment according to claim 2 comprising the nucleotide sequence shown in FIG. 1 of this specification.

4. The DNA segment according to claim 1 wherein said DNA segment is a cDNA segment.

5. The cDNA segment according to claim 4, wherein said cDNA segment is operably linked with an expression vector.

6. The DNA segment of claim 1 wherein said DNA segment encodes an amino acid sequence having the adenylyl cyclase inhibition properties, phosphatidylinositol turnover inhibition properties, $K^+$ channel increase properties, $Ca^{2+}$ mobilization inhibition properties, pharmacological properties, and G regulatory protein coupling properties of a receptor having the amino acid sequence shown in FIG. 1.

* * * * *